United States Patent
Stroïazzo Mougin

(10) Patent No.: US 9,573,875 B2
(45) Date of Patent: Feb. 21, 2017

(54) PROCEDURE FOR THE OBTAINMENT OF FATTY ACIDS OF PHARMACOLOGICAL AND NUTRITIONAL INTEREST

(76) Inventor: Bernard A. J. Stroïazzo Mougin, Alicante (ES)

( * ) Notice: Subject to any disclaimer, the term of this patent is extended or adjusted under 35 U.S.C. 154(b) by 897 days.

(21) Appl. No.: 13/805,421

(22) PCT Filed: Jun. 23, 2010

(86) PCT No.: PCT/ES2010/070424
§ 371 (c)(1),
(2), (4) Date: Mar. 1, 2013

(87) PCT Pub. No.: WO2011/161274
PCT Pub. Date: Dec. 29, 2011

(65) Prior Publication Data
US 2013/0197086 A1 Aug. 1, 2013

(51) Int. Cl.
| | | |
|---|---|---|
| A23L 33/12 | (2016.01) |
| C07C 57/03 | (2006.01) |
| A61K 31/201 | (2006.01) |
| A61K 31/202 | (2006.01) |
| C12P 7/64 | (2006.01) |
| A61K 45/06 | (2006.01) |

(52) U.S. Cl.
CPC ............ *C07C 57/03* (2013.01); *A23L 33/12* (2016.08); *A61K 31/201* (2013.01); *A61K 31/202* (2013.01); *A61K 45/06* (2013.01); *C12P 7/6409* (2013.01); *C12P 7/6427* (2013.01); *C12P 7/6463* (2013.01); *C12P 7/6472* (2013.01); *Y02P 20/582* (2015.11)

(58) Field of Classification Search
None
See application file for complete search history.

(56) References Cited

FOREIGN PATENT DOCUMENTS

EP 2135939 * 12/2009

OTHER PUBLICATIONS

Doughman et al., Omega-3 Fatty Acids for Nutrition and Medicine: Considering Microalgae Oil as a Vegetarian Source of EPA and DHA, Current Diabetes Reviews, 2007, 3, 198-203.*
Hsiao et al., Physiological Studies of Eicosapentaenoic Acid Production in the Marine Microalga Glossomastix chrysoplasta, Biotechnology and Bioengineering, vol. 93, No. 3, Feb. 20, 2006.*

* cited by examiner

*Primary Examiner* — Suzanne M Noakes
*Assistant Examiner* — Stephen Chong
(74) *Attorney, Agent, or Firm* — Ladas & Parry LLP

(57) ABSTRACT

This invention refers to a procedure for obtaining fatty acids of pharmacological and nutritional interest that comprises the steps of feeding a gas comprising $CO_2$ into a reactor that contains a culture that comprises at least one species of microalgae capable of photosynthesis, the process of photosynthesis by the species of microalgae from the $CO_2$ supplied, producing a biomass that contains a general formula (I) compound:

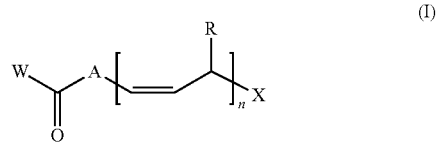

extraction of the general formula (I) compound from the biomass obtained and concentration and/or purification of this compound.

26 Claims, No Drawings

PROCEDURE FOR THE OBTAINMENT OF FATTY ACIDS OF PHARMACOLOGICAL AND NUTRITIONAL INTEREST

RELATED APPLICATION INFORMATION

This application is a 371 of International Application PCT/EP2010/070424 filed 23 Jun. 2010 Entitled "Procedure For The Obtainment Of Fatty Acids Of Pharmacological And Nutritional Interest", which was published on 29 Dec. 2011, with International Publication No. WO 2011/161274 A1.

FIELD OF THE INVENTION

This invention refers to a procedure with the benefit of being industrial and continuous for obtaining fatty acids of pharmacological and nutritional interest that comprises the steps of:
 feeding a gas that comprises at least $CO_2$ as well as greenhouse gases, into a reactor that contains a culture that comprises at least one species of microalgae capable of photosynthesis;
 photosynthesis by the species of microalgae from the $CO_2$ supply, producing a biomass that contains a general formula (I) compound:

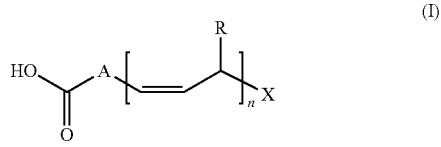

extraction the general formula (I) compound from the biomass obtained; and
 concentration and/or purification of the general formula (I) compound.

Furthermore, this invention refers to the compounds of pharmacological and nutritional interest obtained from the invention procedure that uses microalgae and carbon dioxide as source for obtaining them.

PREVIOUS STATE OF THE ART

Cardiovascular diseases (CVD) are the main cause of death worldwide. More people die every year from cardiovascular disease than any other cause. It is calculated that in 2005, 17.5 million people died of this cause, representing 30% of all deaths recorded in the world; 7.6 million of these deaths were due to coronary heart disease, and 5.7 due to cerebrovascular accidents (CVA). Deaths due to CVD affect both sexes equally, and more than 80% occur in countries with low or average incomes. It is calculated that in 2015, around 20 million people will die of CVD, especially heart disease and CVA, and it is expected to continue being the main cause of death.

Heart attacks and CVAs are usually acute phenomena mainly caused by obstructions preventing blood flow to the heart or brain. The most frequent cause is the formation of fat deposits on the walls of the blood vessels that irrigate the heart and brain. CVAs may also be caused by haemorrhages in cerebral blood vessels or blood clots.

The causes of CVD are well defined and well known. The most important causes of heart disease and CVD are known as "modifiable risk factors": unhealthy diet, physical inactivity and smoking. The effects of unhealthy diet and physical inactivity may appear as "intermediate risk factors": increased blood pressure and sugar and fat levels in the blood, excess weight and obesity. The modifiable risk factors are responsible for approximately 80% of cases of coronary heart disease and cerebrovascular accident.

There are also a number of underlying factors for chronic diseases, i.e., 'causes of causes', which are a reflection of the main forces that affect social, economic and cultural changes: globalisation, urbanisation and an aging population. Other factors affecting CVD are poverty and stress.

At least 80% of premature deaths due to heart disease and CVD could be prevented through a healthy diet, regular physical activity and giving up smoking. It is possible to reduce the risk of CVD through regular physical activity, avoiding active or passive inhalation of tobacco smoke, consuming a diet rich in fruit and vegetables, avoiding food with a high fat, sugar and salt content and maintaining a healthy body weight. The way to prevent and control CVD is through global, integrated action:

Global action requires a combination of measures that aim to reduce the total risk among the population and strategies aimed at high-risk individuals or those who suffer from the disease.

Examples of population-level interventions to reduce CVD are global policies to control smoking, taxes to reduce consumption of food rich in fats, sugars and salts, the creation of pedestrian and cycle paths to promote physical activity and the supply of healthy foods in school dining rooms.

Integrated strategies focus on the main risk factors common to chronic diseases such as CVD, diabetes and cancer: unhealthy diet, physical inactivity and smoking. In this context, see, for example: http://www.who.int/mediacentre/factsheets/fs317/es/index.html In accordance with the above, an integrated strategy would involve encouraging consumption of omega-3 fatty acids (referred to hereinafter simply as 'omega-3'); it has been shown experimentally that the consumption of large amounts of omega-3 considerably increases blood clotting time, which explains why the incidence of cardiovascular diseases is notably low among communities with diets high in omega-3 (Inuit, Japanese, etc.); see '*Marine oils as a source of omega-3 fatty acids in the diet: how to optimize the health benefits*", Uauy Dagach, R: Valenzuela, A. *Prog-Food-Nutr-Sci.* 1992; 16(3): 199-243; "*Fish Consumption, Fish Oil, Omega-3 Fatty Acids, and Cardiovascular Disease*", Penny M. Kris-Etherton, PhD, RD; William S. Harris, PhD; Lawrence J. Appel, MD, MPH, for the Nutrition Committee, *Circulation.* 2002; 106:2747-2757; "*The Effect of Dietary {omega}-3 Fatty Acids on Coronary Atherosclerosis*", Clemens von Schacky, MD; Peter Angerer, MD; Wolfgang Kothny, MD; Karl Theisen, MD; and Harald Mudra, MD, *Annals of Internal Medicine,* 6 Apr. 1999|Volume 130 Issue 7| Pages 554-562.

Some experiences also suggest that omega-3 consumption has beneficial effects on the brain. High amounts could reduce the effects of depression "*Omega* 3 *Fatty Acids in Bipolar Disorder*", Andrew L. Stoll, *Arch Gen Psychiatry.* 1999; 56:407-412; "*Addition of Omega-3 Fatty Acid to Maintenance Medication Treatment for Recurrent Unipolar Depressive Disorder*", Boris Nemets, *Am. J. Psychiatry* 159:477-479, March 2002 and even groups of school-age children notably improved their performance after ingesting fish-oil tablets (rich in omega-3).

However, caution is required on ingesting fish oils as a food supplement, due to the risk of consuming dangerous amounts of dioxins, mercury and other heavy metals present in many types of fish.

The best sources of omega-3 are cold-water fish, including salmon, which supposedly has the lowest levels of contamination. Other important sources include blue fish, among them the sardine, which has a ratio of 1:7 omega-6 to omega-3.

The best alternative among vegetables is hemp seed, as it has the ideal percentage of omega-6 and omega-3: three parts omega-6 to one part omega-3 (3/1); furthermore, the seeds are cheap in pet-food shops, but have a very hard husk, so consumption is very unpleasant.

Omega-3 fatty acid compounds can be used to reduce triglycerides as an alternative to a fibrate and added to a statin in patients with combined (mixed) hyperlipidemia not controlled by a statin alone. Triglycerides concentrations of more than 10 mmol/l are associated with acute pancreatitis; thus a reduction in concentration reduces the risk. The fat content in the components of omega-3 fatty acids (including their excipients) should be born in mind during treatment for high triglyceride levels.

Omega-3 fatty acids are known as essential fatty acids as the human body cannot produce them by itself. Chemically, they are long-chain polyunsaturated fatty acids (PUFAs) with multiple double carbon-carbon bonds, with the first of its double bonds in the third carbon from the termination methyl group.

These omega-3 acids are known to have anti-inflammatory functions (improving the immune response) and are effective in the prevention and treatment of certain heart diseases, in controlling the amount of triglycerides in the blood and in preventing heart attacks, thrombi and similar conditions, as well as having beneficial effects on the nervous and digestive systems. Numerous studies have been performed showing these essential fatty acids can benefit patients with arthritis, high blood pressure, neuro-dermatitis and other conditions.

Although we are only beginning to understand the biological functions of these PUFAs, their impact on health means they are critical nutrients and a general consensus is forming that they should become daily supplements in all diets. In response partly to these clinical results, many international institutions and authorities now recommend increasing daily consumption of these compounds.

This sudden pharmaceutical and nutritional interest has led to an explosion of demand for PUFAs, which, combined with the insufficient supply from traditional sources and inadequate supply of high-purity PUFAs for biomedical use (nutritional-pharmaceutical quality) has produced a search for alternative sources, such as fungi and bacteria.

As well as the group of fatty acids comprising the omega-3 complex, those comprising the omega-7 and 9 groups are also considered of vital importance. Omega-7, or palmitoleic acid, is highly beneficial to the skin and mucosas, and is present in considerable concentrations in both tissues. It is a monounsaturated fatty acid present in a proportion of 28% in the oil of a shrub known as sea-buckthorn (*Hippophae rhamnoides*). This plant grows in China and on the European Atlantic coast in the form of a shrub, and its berries (seeds and pulp) are used to produce the oil. Traditionally, sea-buckthorn oil has been used to treat various epithelial diseases.

The functions of omega-7 in the skin and mucosas are:
Anti-inflammatory: helps alleviated or improve the symptoms of certain skin conditions, such as dermatitis, eczema and psoriasis, and mucosa conditions, such as gastric and peptic ulcers, and acts in vaginal inflammation, among other conditions.

Mild analgesic: acts on the pain caused by skin and mucosa conditions.

Antioxidant: provides protection from certain substances, such as free radicals.

Nutrient: for both the skin and the mucosas.

Omega-9 (ω-9) fatty acids are a type of unsaturated fatty acid found in some foods. Some studies suggest these fatty acids are related to breast cancer (Valeria Pala, Vittorio Krogh, Paola Muti, Véronique Chajès, Elio Riboli, Andrea Micheli, Mitra Saadatian, Sabina Sieri, Franco Berrino (2001). The biological effects of ω-9 are generally mediated by its interactions with omega-3 and omega-6 fatty acids; they have a double C=C bonds in the ω-9 position. Some ω-9's are common components of animal fat and vegetable oil.

Two important ω-9 fatty acids son:
Oleic acid (18:1 ω-9), which is the main component of olive oil and other monounsaturated fats.
Erucic acid (22:1 ω-9) found in rapeseed (*Brassica napus*), wallflower (Erysimum) seeds and mustard (Brassica) seeds. Rapeseed with a high erucic acid content are used commercially in paints and varnishes as a drying and protecting agent.

Unlike the ω-3 and ω-6 fatty acids, ω-9 fatty acids are not classified as essential fatty acids (EFAs). This is because they can be synthesised by the human body, so they are not essential in the diet, and because the lack of a ω-6 double bond means they are involved in reactions that produce eicosanoids.

Under severe conditions of EFA deficiency, mammals lengthen and desaturate oleic acid to product eicosatrienoic acid (20:3 ω-9)[2]. This also occurs to a lesser extent in vegetarians and semi-vegetarians (Phinney, S D, R S Odin, S B Johnson and R T Holman (1990).

The marketing of fatty acids with pharmacological properties of interest produced from microalgae oils depends on its competitiveness with fish oils. The choice of a particular source is based on the required concentration of PUFAs, the availability of the raw material and the presence and nature of impurities.

Normally, omega-3 fatty acids are consumed in two ways: through daily diet and/or as a food supplement. Today, the main source of dietary omega-3 fatty acids is fish. However, the growing pharmaceutical and nutritional demand, added to a series of inconveniences relating to these types of acids, which in many cases can be resolved by using another type of oil (microalgae), have created the need for new paths of research into alternative sources. In this context, microalgae represents an alternative source, both in terms of global production and product quality.

In accordance with the above, some of the inconveniences of fish oil are described below and the extent to which the product extracted from microalgae represents a solution to these inconveniences is discussed.

Fish oils contain varying amounts of omega-3 fatty acids in general; however, the concentration of the required fatty acids is quite low, given that only a part of the triglycerides contain these fatty acids, so these oils are less beneficial to health, with a high fat and calorie content.

Algae oils, however, contain considerably higher levels of the required acids, with simpler and more homogenous lipid profiles. These organisms are rich in proteins, oligoelements, vitamins, antioxidants, etc. and may be used as sources of macro- and micro-nutrients in food formulations.

Oxidation problems: fish oil contains amounts of short-chain and other highly unsaturated fatty acids, as well as omega-3. The double bonds in the fatty acid chains of both omega-3 and other PUFAs in fish oil are susceptible to oxidation due to oxygen and other oxidising agents. The deterioration of the oil due to oxidation and the action of bacteria during storage can lead to the appearance of low-molecular-weight compounds, such as ketones and aldehides, producing undesirable colours, flavours and/or odours, thus reducing the commercial value of the oil.

Fish oils are also an excellent source of vitamin A and D (especially cod-liver oil), but this could be a problem if the daily recommended dose of vitamins A and D is exceeded in order to consume therapeutic amounts of EPA and DHA. These vitamins are soluble in fat, so it is possible that a dietary excess (much higher than the recommended daily dose) is accumulated in the organism and can become harmful.

Fish oil varies in price and quality (seasonal). However, in the case of oil from microalgae, production can carry on throughout the year, as there is normally no seasonal (climatic) or nutritional dependence, especially if the culture system is a closed circuit (in photobioreactors, such variables can be controlled).

Contaminants such as pesticides and heavy metals may be present. Some sources urge caution when taking cod-liver oil and other supplements made from fish as they are increasingly likely to contain high levels of toxins, such as mercury and PCBs.

Unfortunately, currently most fish is contaminated with mercury, other metals such as cadmium, lead, chrome or arsenic, PCB, dioxins and other toxins. The greatest concern is contamination by mercury, a metal that is highly toxic to humans. In the US alone, 40 tonnes of mercury are emitted into the atmosphere every year, which is deposited in water by rain. Although in Spain this issue is largely unmentioned due to the importance of the fishing industry to the economy, in other countries the health authorities have issued warnings on this problem. In the US, the Environmental Protection Agency (EPA) recommends that pregnant women avoid ingesting fish such as tuna, swordfish and other large fish species, as methyl-mercury easily crosses the placental barrier. However, the health benefits of fish to other population groups are considered superior to the risks.

Furthermore, pesticides and herbicides used in conventional agriculture, as well as many other industries, contribute to mercury contamination of seas and oceans.

Obviously, the cultivation of algae, as it is controlled cultivation in a closed system, does not contain mercury or any other type of heavy metal or contaminant.

Characteristic smell. Fish oils contain fatty acids that can be obtained as sub-products in the manufacture of products such as low-fat fish meats. The methods used for extracting and obtaining fish oil usually produce volatile amines, which are substances with an unpleasant odour (trimethylamine, dimethylamine and ammonium). Trimethylamine is one of the main volatile amines associated with the typical fish smell. This is produced by enzyme conversion of trimethylamine oxide, which is an osmoregulatory compound found in many fish. After extraction and storage, the generation and mixing of this unpleasant smell cannot be avoided.

To prevent the emission of such odours there are conventional methods involving refining treatments such as deacidification and deodorisation to eliminate impurities. However, these conventional methods can eliminate some of the some of the odour-causing compounds, but it is impossible to eliminate the volatile amines, the aldehydes and the ketones completely, given that these compounds are the result of greater subsequent degradations that take place during storage. Furthermore, these compounds have a very low odour threshold, which can be quickly detected at very low concentrations.

Most fish oil is used in producing butter or margarine, thus this source is not sufficient for competing in several markets at once.

They have a complex fatty acid profile (up to 50 different fatty acids may be present). In the case of cod-liver oil, almost 30% of the esters are of no interest and have to be separated from the required compound, which makes it difficult to efficiently isolate a specific PUFA (EPA in this case) using simple separation methods. In contrast to fish oil, many microalgae and, specifically, the species used in this invention have a high percentage of EPA content without the presence of very similar PUFAs.

Currently available technologies for purifying individual PUFAs, such as EPA from fish-oil ester concentrates, are based on the physicochemical differences in the compounds. These differences are usually associated with the number of double bonds and the length of the chain. The higher the number of compounds similar to the required compound that are present in the sample, the harder it is to isolate the PUFA. Generally, fish oils contain a mixture of many metabolically active fatty acids, so new sources that provide a single bioactive fatty acid in high concentrations are required. In this context, microalgae have a much simpler fatty acid profile than fish oil, so that, using the same purification technique it is possible to obtain a greater yield and purity if a microalgae extract is used instead of a fish oil.

Therefore, as described above, simpler, less contaminating methods for producing such compounds of pharmacological and nutritional interest than those produced from fish oil are necessary. In this sense, this invention describes a new procedure for the production of these compounds in a simple, non-contaminating, environmentally-friendly, high-yield and highly profitable way compared to currently used means.

DESCRIPTION OF THE INVENTION

This invention refers to an accelerated procedure, with the advantages of being industrial and continuous, for obtaining fatty acids of pharmacological and nutritional interest. Furthermore, this invention refers to the compounds of pharmacological and nutritional interest obtained from the industrial, continuous procedure that uses microalgae and carbon dioxide, preferably from industrial emissions, as a source for obtaining them.

Also, this invention refers to the use of compounds obtained to prevent diseases of the cardiovascular, nervous, autoimmune and digestive systems.

Therefore, a first aspect of this invention refers to a procedure for obtaining fatty acids of pharmacological and nutritional interest that comprises the steps of:

a) feeding a gas or a mixture of gases that comprises $CO_2$ into a reactor that contains a culture that comprises at least one species of microalgae capable of photosynthesis;

b) photosynthesis by the species of microalgae using the $CO_2$ supplied, producing a biomass that contains a general formula (I) compound:

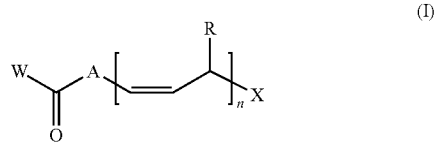

where:

A and X are equal or different independently and are selected from alkyl $C_3$-$C_{10}$, alkenyl $C_1$-$C_{10}$, cycloalkyl $C_1$-$C_7$ or any substituted or unsubstituted aryl group;

n is a integer from 1 to 10;

R is selected from H, a hydroxyl group, alkyl $C_1$-$C_4$, alkenyl $C_1$-$C_3$, cycloalkyl $C_3$-$C_7$ or any other substituted or unsubstituted aryl;

W is selected from the group that consists of a hydroxyl group, a glycerol molecule bound to an additional general formula (I) compound forming a diglyceride, or a glycerol molecule bound to two additional general formula (I) compounds forming a triglyceride;

and their salts, preferably any pharmaceutically acceptable salt, solvate or their prodrugs;

c) extraction of the general formula (I) compound from the biomass obtained in step b); and d) concentration and/or purification of the general formula (I) compound obtained in step c);

characterised in that after the photosynthesis steps, between 5 and 100% of the culture is removed from the reactor, which is then separated in a solid fraction that contains biomass, which then undergoes the step of extraction of the general formula (I) compound and a liquid fraction that contains carbonates and/or bicarbonates, which are separated from the liquid fraction to at least partially return the liquid fraction, substantially free of carbonates and/or bicarbonates, to the reactor.

In general, the procedure for obtaining the fatty acid with pharmacological and nutritional activity from the general formula (I) comprises the steps of:

uptake of a gas or mixture of gases that contains $CO_2$;

assimilation and transformation of the $CO_2$ by the microalgae, producing a biomass that contains the general formula (I) compound;

mechanical treatment of the culture medium;

mechanical-chemical treatment of the aqueous phase;

extraction of the general formula (I) compound; and concentration and/or purification of the general formula (I) compound.

Step of Uptake of a Gas or Mixture of Gases that Contains $CO_2$

In a preferred embodiment, the step of uptake of a gas or mixture of gases containing $CO_2$, such as greenhouse gasses, comprises the endogenous and/or exogenous feed of such a gas or mixture of gases into a photosynthetic type reactor in which there is at least one species of microalgae capable of photosynthesis.

In this same method, throughout this descriptive report, 'greenhouse gases' are understood to be any gas that comprises $CO_2$. Normally, these gases consist of a mixture that contains $CO_2$ and other potential components such as $NO_x$, $CH_4$ or others, in any combination. However, the only truly necessary element for the procedure of the invention is that it contains at least $CO_2$.

Thus, these gases that are so harmful to the environment become part of the nutrients added to the reactor to 'feed' the microalgae inside.

Also, the greenhouse gases added exogenously normally come from the atmosphere or industry and those added endogenously come from gases generated in the procedure developed in this invention.

Depending on the composition of these gases, they optionally undergo prior treatment before being added to the system, in the photobioreactors; basically this treatment consists of at least one of the following: substantial elimination of $SO_x$, $NO_x$ and moisture, and adjusting the temperature of the gases to 30-40° C.

Beneficially, the procedure of the invention is a continuous industrial procedure that functions under axenic conditions, i.e. isolated from external contamination.

Step of Assimilation and Transformation of the $CO_2$ by the Microalgae, Producing a Biomass that Contains the General Formula (I) Compound As per another preferred embodiment, the step of assimilation and transformation of the $CO_2$ comprises the photosynthesis process in accordance with the photosynthetic nature of the microalgae; to this end the reactor containing them is continually exposed to natural or artificial light, or any combination of both.

Thus, the microalgae in the reactors are capable of assimilating the carbon present in carbon dioxide. In accordance with this assimilation and thanks to the provision, preferably, of other nutrients in lower proportions, such as nitrates, phosphates and trace metals, the microalgae are capable of generating more complex structures: proteins, carbohydrates and lipids, among others, although these are the main ones. Within the group consisting of the lipids are the general formula (I) compounds, so that this $CO_2$ is transformed by the photosynthetic action of the microalgae into biomass that contains the general formula (I) compound, ready for passing on to the next step of the procedure.

Furthermore, to improve the efficiency of the uptake of these greenhouse gases by the microalgae, the interior of the photosynthetic reactors can be worked with turbulence. The main purpose of this turbulence it to force every individual (every microalgae) into contact with the light for the maximum time possible. Furthermore, the turbulence helps prevent the formation of fouling. Any appropriate method may be used to generate the turbulence, although normally air, $N_2$, $CO_2$, CO, $NO_x$, combustion gases or any combination of them are pumped in.

Also, the microalgae in the reactor is preferably selected from a group consisting of: *Clorophyceae, Bacilliarioficeas, Dinophyceae, Cryptophyceae, Chrysophyceae, Haptophyceae, Prasinophyceae, Raphidophyceae, Eustigmatophyceae* or any combination of these. These species of microalgae are those that have been shown to be capable of satisfactorily producing fatty acids of pharmacological and nutritional interest obtained as per the procedure of the invention.

In accordance with the above, the carbon from the greenhouse gases is transformed in this step into among others substances, general formula (I) fatty acids, after which the next step is carried out.

Step of Mechanical Treatment of the Culture Medium

As per another preferred embodiment, the step of mechanical treatment of the culture medium comprises the sub-steps of:

emptying or at least partially removing the culture from the reactor;

separation of the culture removed in a solid fraction that contains biomass and a liquid fraction that contains carbonates and/or bicarbonates;

As per another preferred embodiment, in the emptying sub-step, between 5 and 100% of the culture medium, preferably between 5 and 50% and even more preferably 10%, of the culture medium is removed, so that the rest stays in the reactor to continue the continual uptake and conversion of $CO_2$ by means of microalgae as a biological medium for this purpose. It is important to emphasise that this extraction percentage is replaced, preferably quickly, with water substantially without or with very low concentrations of algae and carbonates that comes from the separation steps described below; the amount of algae present in the water that is returned depends on the efficiency of separation of each specific method.

As per another preferred embodiment, the sub-step of separation of the removed culture in a solid fraction that contains biomass and a liquid fraction that contains carbonates and/or bicarbonates comprises at least one mechanical extraction phase selected from filtration, centrifugation, flocculation, electrocoagulation, ultrasounds, evaporation, decantation or any combination of these. Thus the aqueous phase is separated from the biomass.

As per another optional preferred embodiment, after the emptying phase, a phase of acidification of the culture medium removed or extracted from the reactor is carried out. In this optional sub-step, the removed or extracted culture medium is collected in an collection tank, in which at least one acidifying agent is added to obtain a pH of between 3.5 and 8, preferably between 6 and 8. The acidifying agent is selected from a group consisting of $CO_2$ (this $CO_2$ may be bottled or industrial), a mixture of $CO_2$ and air, strong and weak acids or any combination of these. Preferably, the acidifying agent is a mixture of $CO_2$ with air. Thus, the medium from the reactor, which is rich in $CO_2$ and bicarbonate is prevented from precipitating (by the non-formation of carbonates) and thus the phenomena of adherence and fouling are avoided.

Step of Mechanical-Chemical Treatment of the Aqueous Phase

As per another preferred embodiment, the step of chemical treatment of the aqueous phase comprises the following sub-steps:
chemical conversion of the $CO_2$ present in the liquid fraction resulting from the removal of at least part of the culture from the reactor in the form of carbonates and/or bicarbonates in dissolution, in their corresponding precipitated carbonated forms, by means of the addition of an alkali, and
recirculation of at least part of the liquid phase, already substantially free of carbonates and/or bicarbonates in dissolution, to the reactor;

Thus, as per another preferred embodiment, the sub-step of chemical conversion of $CO_2$ comprises carrying the water resulting from the sub-step of separation of biomass from the aqueous phase to a clarification tank which collects the aqueous phase, comprising water, nutrients in dissolution, $CO_2$, carbonate and bicarbonate, all of them dissolved. Once the aqueous phase is in the clarification tank, at least one basic medium is added to provoke precipitation in the form of carbonates of the species in equilibrium ($CO_2$, bicarbonate and carbonate). Thus, it is possible to eliminate even more $CO_2$, as it is transformed into non-contaminating carbonated salts used in different industries.

Once the water is free of $CO_2$, precipitated in the form of carbonate and bicarbonate, the step of recirculating the water to the reactor containing the culture medium is carried out.

Thus, at this point in the procedure, double elimination or conversion of $CO_2$ has been conducted: the uptake or biological binding carried out by the microalgae in the culture medium, and a chemical conversion or transformation as a consequence of this precipitation. By doing this, the culture water contains even less $CO_2$, bicarbonate and carbonate and can take up more $CO_2$ until the solubility limit is exceeded. During the following cycle, the procedure is again conducted, ending with the precipitation of most of the $CO_2$ that has been added. If this forced precipitation does not take place, most of the $CO_2$ remains dissolved in the aqueous phase returned to the culture. Therefore, when adding $CO_2$ to the culture again, the dissolution capacity will be less, as there is already $CO_2$ in the solution.

Step of Extraction of the General Formula (I) Compound

As per another preferred embodiment, the step of extraction of a general formula (I) compound,

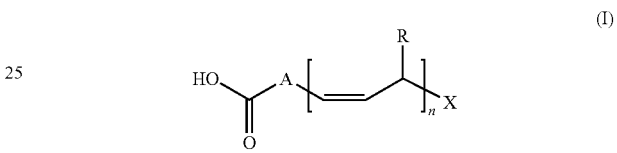

refers to the process in which, once these compounds have been produced by the microalgae, they are extracted from the biomass obtained in the $CO_2$ assimilation and transformation phase. The biomass obtained normally has a moisture content of between 1-99%, preferably between 65-80%.

Once the biomass is available, the general formula (I) compound is extracted. This extraction may be carried out in two ways:
Extraction of the complete lipid fraction; in this case, as a consequence of polarity, all the apolar fraction is extracted.
Selective extraction of the compound of interest.

The extraction of the lipid fraction or the selective extraction of the compound of interest is carried out by means of one, various, or a combination of the following methods:
Extraction with solvents selected from the group consisting of isopropanol, hexane, heptane, methanol, ethanol, dichloromethane, acetone, water, chloroform, butyl acetate, tetrahydrofuran, 2-methyltetrahydrofuran, butanol, toluene, benzene or any combination of these;
Extraction using $CO_2$ as a solvent under supercritical conditions: pressure consisting of 100 to 300 bar, preferably 180 to 220 bar, the temperature being 25 to 350° C., preferably 40 to 80° C.

Before this extraction step, a sub-step may be carried out to produce lysis or disruption of the algae. This prior sub-step may be carried out by at least one of the following techniques:
Ultrasound treatment: to do this, the algae is subjected to frequencies between 100-1,000 Hz, preferably between 300-400 Hz, the time for this application being between 1 min and 25 min, preferably between 2-10 min.
Homogenisation or cavitation: the microalgae are subjected to a pressure of between 1 and 2,500 bar, preferably between 250-1,200 bar. This procedure may be repeated various times to produce cell disruption; normally the number of cycles is between 1 and 5, preferably 1.

Treatment by lowering or raising pH. Disruption of the algae is obtained as a consequence of raising pH to above 9 (basic strong or weak, organic or inorganic agents) or below 6 (strong or weak, organic or inorganic agents).

Step of Concentration and/or Purification of the General Formula (I) Compound

As per another preferred embodiment, the step of concentration and/or purification of the general formula (I) compound is carried out by any method suitable for this purpose, although preferably by the use of at least one of the techniques that are selected from a group consisting of molecular or fractional distillation, enzyme division, supercritical extraction with $CO_2$, crystallisation at low temperature, adsorption chromatography and precipitation with urea. The purification is achieved as a consequence of concentration of the product in question.

A second aspect of this invention refers to a general formula (I) compound obtained by means of the procedure described above. This compound has the following structure:

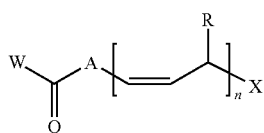

where:

A and X are equal or different independently and are selected from alkyl $C_3$-$C_{10}$, alkenyl $C_1$-$C_{10}$, cycloalkyl $C_1$-$C_7$ or any substituted or unsubstituted aryl group;

n is a integer from 1 to 10;

R is selected from H, a hydroxyl group, alkyl $C_1$-$C_4$, alkenyl $C_1$-$C_3$, cycloalkyl $C_3$-$C_7$ or any other substituted or unsubstituted aryl;

W is selected from the group that consists of a hydroxyl group, a glycerol molecule bound to a general formula (I) compound forming a diglyceride, or a glycerol molecule bound to two general formula (I) compounds forming a triglyceride;

and their salts, preferably any pharmaceutically acceptable salt, solvate or their prodrugs;

In a preferred embodiment, A and X may be equal or different independently and are selected from alkyl $C_1$-$C_8$, alkenyl $C_1$-$C_5$ and cycloalkyl $C_4$-$C_6$.

In a preferred embodiment, n is a integer selected from 1 to 7.

In another preferred embodiment, W is OH or a glycerol group bound to two general formula (I) compounds, forming a triglyceride.

In a further preferred embodiment, R is selected from H, a hydroxyl group, alkyl $C_1$-$C_4$ and cycloalkyl $C_4$-$C_6$.

The term 'alkyl' in this invention refers to hydrocarbon-, linear- or branched-chain radicals, that have from 1 to 10 carbon atoms, preferably 1 to 4, and which bind to the rest of the molecule by a single bond, e.g. methyl, ethyl, n-propyl, i-propyl, n-butyl, terc-butyl, sec-butyl, n-pentyl, n-hexyl, etc. The alkyl groups may optionally be replaced by one or more substitutes, such as halogen, hydroxyl, alkoxyl, carboxyl, carbonyl, cyano, acyl, alkoxycarbonyl, amine, nitro, mercaptan and alkylthiol.

The term 'alkenyl' refers to hydrocarbon-chain radicals that contains one or more double carbon-carbon bonds, e.g. vinyl, 1-propenyl, allyl, isopropenyl, 2-butenyl, 1,3-butadienyl, etc. The alkenyl radicals may optionally be replaced by one or more substitutes, such as halo, hydroxyl, alkoxyl, carboxyl, cyano, carbonyl, acyl, alkoxycarbonyl, amine, nitro, mercaptan and alkylthiol.

In another preferred embodiment, the general formula (I) compound refers to a compound that is selected from the following group:

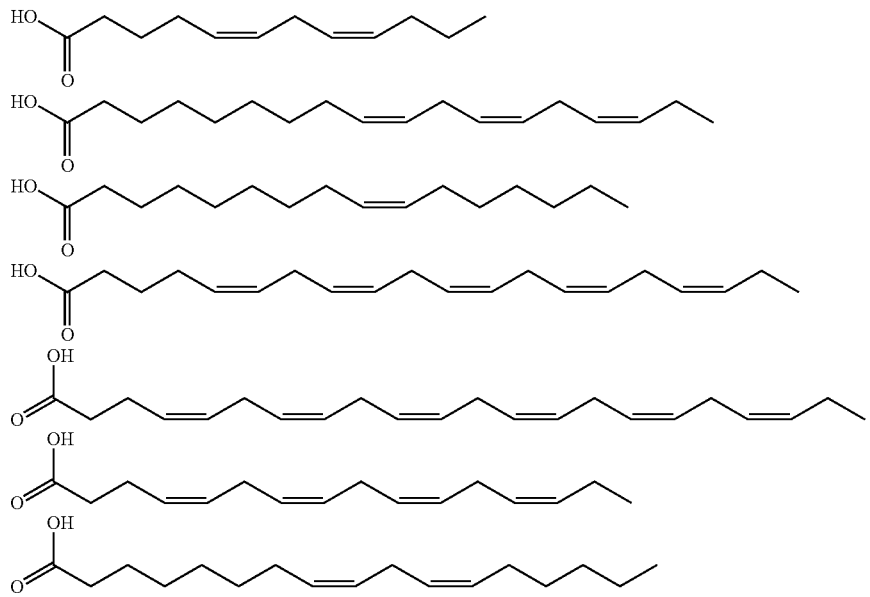

or an isomer, a pharmaceutically acceptable salt, a prodrug or its solvate.

The compounds represented by formula (I) may include isomers, depending on the presence of multiple bonds, including optical isomers or enantiomers, depending on the presence of chiral centres. Individual isomers, enantiomers or diastereoisomers and the mixtures of them fall within the scope of this invention, i.e. the term isomer also refers to any mixture of isomers, such as diastereomers, racemic mixtures, etc., including their optically active isomers or mixtures of them in different proportions. Individual enantiomers or diastereoisomers, as well as their mixtures, may be separated using conventional techniques.

Furthermore, within the scope of this invention are the prodrugs of the formula (I) compound. The term prodrug as used here includes any compound derived from a formula (I) compound, e.g.: esters (including carboxylic acid esters, amino acid esters, phosphate esters, metal salt sulfonate esters etc.), carbamates, amides, etc. which when administered to an individual may be transformed directly or indirectly into formula (I) compound in the individual. Beneficially, this derivative is a compound that increases bioavailability of the formula (I) compound when it is administered to an individual, or which strengthens the release of the formula (I) compound in a biological compartment. The nature of this derivative is not critical as long as it can be administered to an individual and provide the formula (I) compound in a biological compartment of the individual. This prodrug may be prepared by means of conventional methods known by experts in the field.

The compounds of the invention may be in crystalline form, such as free compounds or solvates. In this sense, the term 'solvate' as used here includes both pharmaceutically acceptable solvates, i.e. solvates of the formula (I) compounds that can be used in preparing a drug, and pharmaceutically unacceptable solvates, which can be used in the preparation of solvates or pharmaceutically acceptable salts. The nature of the pharmaceutically acceptable solvate it not critical as long as it is pharmaceutically acceptable. In a specific embodiment, the solvate is a hydrate. The solvates may be obtained by conventional solvation methods known by experts in the field.

For their application in therapy, the formula (I) compounds, their salts, prodrugs or solvates are, preferably, in a pharmaceutically acceptable or substantially pure form, i.e. they have a pharmaceutically acceptable level of purity, excluding normal pharmaceutical additives such as diluents and carriers and not including materials considered toxic at normal dosage levels. The levels of purity for the active ingredient are preferably higher than 50%, and more preferably higher than 70% and even more preferably higher than 90%. In a preferred embodiment, they are higher than 95% of the formula (I) compound or its salts, solvates or prodrugs.

In another preferred embodiment, the general formula (I) compound is used as a drug.

In another preferred embodiment, the general formula (I) compound is used as a nutritional supplement.

In another aspect, this invention also refers to the pharmaceutical compositions that comprise at least one compound of the invention, a tautomer, a pharmaceutically acceptable salt, a derivative or its prodrug, together with a pharmaceutically acceptable carrier, an excipient or a vehicle, for administration to a patient.

In a preferred embodiment, the pharmaceutical composition also comprises another active ingredient.

The adjuvants and pharmaceutically acceptable vehicles that can be used in these compositions are the adjuvants and vehicles known by technicians in the field and commonly used in the elaboration of therapeutic compositions.

In the meaning used in this description, the expression 'therapeutically accepted amount' refers to the amount of the agent or compound capable of developing the therapeutic action determined by its pharmacological properties, calculated to produce the desired effect and, in general, is determined, among other factors, by the characteristics of the compounds, including the age and state of the patient, the severity of the condition or disorder and the form and frequency of administration.

The compounds described in this invention, their salts, prodrugs and/or solvates, as well as the pharmaceutical compounds that contain them, may be used together with other additional drugs or active ingredients to provide a combination therapy. These additional drugs may be part of the same pharmaceutical composition or, alternatively, may be provided in the form of a separate composition for simultaneous or non-simultaneous administration from the pharmaceutical composition that comprises the formula (I) compound, or its salt, prodrug or solvate.

In a preferred embodiment of this invention, the pharmaceutical compositions are adequate for oral administration, in solid or liquid form. The possible forms for administration are tablets, capsules, syrups or solutions and may contain conventional excipients known in the pharmaceutical field, such as aggregants (e.g. syrup, acacia, gelatine, sorbitol, tragacanth or polyvinylpyrrolidone), fillers (e.g. lactose, sugar, corn starch, calcium phosphate, sorbitol or glycine), disintegrating agents (e.g. starch, polyvinylpyrrolidone or microcrystalline cellulose) or a pharmaceutically acceptable surfactant such as sodium lauryl sulphate.

The compositions for oral administration may be prepared by conventional Galenic pharmacy methods, such as mixing and dispersing. The tablets can be coated following the known methods in the pharmaceutical industry.

The pharmaceutical compositions may be adapted for parenteral administration, such as sterile solutions, suspensions and freeze-dried products of the invention, using the appropriate dose. Appropriate excipients may be used, such as pH buffering agents or surfactants.

The abovementioned formulations may be prepared using conventional methods, such as those described in different countries' pharmacopoeias and other reference texts.

The compounds or compositions of this invention may be administered by means of any adequate method, such as intravenous infusion or oral, intraperitoneal or intravenous administration. Oral administration is the preferred form due to its convenience to patients and due to the chronic nature of the diseases being treated.

The amount of a compound administered in this invention will depend on the relative efficacy of the chosen compound, the severity of the disease to be treated and the weight of the patient. However, the compounds in this invention will be administered one or more times daily, e.g. 1, 2, 3 or 4 times daily, with a total dose of between 0.1 and 1,000 mg/kg/day. It is important to bear in mind that it might be necessary to introduce variations in the dose, depending on the age and condition of the patient, as well as modifications in the form of administration.

The compounds and compositions of this invention may be employed together with other drugs in combined therapies. Other drugs may be part of the same composition or another different composition, for their administration at the same or different times.

Another essential aspect of this invention refers to the use of at least one formula (I) compound for the manufacture of a drug for the treatment and/or prophylaxis of a cardiovascular, digestive, nervous or immune system disease.

Another aspect of this invention refers to the use of at least one formula (I) compound for the manufacture of a drug for the prevention and/or treatment of diabetes mellitus, Crohn's disease, ulcerative colitis, intermittent claudication, cardiovascular diseases, cystic fibrosis, bipolar disorder, dementia and schizophrenia.

Throughout the description and claims, the word "comprises" and its variants are not intended to exclude other technical characteristics, additives, components or steps. For experts in the material, other objects, advantages and characteristics of the invention are given in the descriptive and practical sections of the invention. The following examples are provided by way of illustration, and are not supposed to be limiting for this invention.

EXAMPLES OF EMBODIMENT

Below are a series of examples that are, at all times, described to illustrate the synthesis of some specific components of this invention and to exemplify the general procedures. In accordance with the above, the following section of examples is in no way intended to limit the scope of the invention discussed in this descriptive report.

In this descriptive report, the symbols and conventions used in these procedures, diagrams and examples are consistent with those used in the international system and the contemporary scientific literature, e.g. the Journal of Medicinal Chemistry. Except where otherwise indicated, all the starting materials were obtained from commercial suppliers and were used without additional purification. Specifically, the following abbreviations may be used in the examples and throughout the descriptive report: g (grams); mg (milligrams); kg (kilograms); µg (micrograms); L (litres); mL (millilitres); µL (microlitres); mmol (millimoles); mol (moles); ° C. (degrees Celsius); Hz (hertz); MHz (megahertz); δ (chemical displacement); s (singlet); d (couplet); t (triplet); q (quartet); m (multiplet); RMN (nuclear magnetic resonance); M (molar); $Et_3N$ (triethylamine); DMF (dimethylformamide); DMSO (dimethyl sulfoxide); ACN (acetonitrile); PBS (saline buffer phosphate).

Example Number 1

Obtaining EPA

The starting point is the uptake of greenhouse gases resulting from combustion in a cement factory, these emissions being:

| | |
|---|---|
| Temperature | 150° C. |
| Pressure | 1 bar |
| Density | 0.77 kg/m3 |
| Mass flow | 43,914 kg/h |
| Specific heat | 0.25 kcal/kg |
| Volumetric flow | 57,377 m³/h |
| $CO_2$ | 6% V |
| $N_2$ | 67.6% V |
| $O_2$ | 2.1% V |
| $H_2O$ | 20.7% V |
| $CH_4$ | 9,000 ppm |
| $NO_x$ | 50 ppm |
| $SO_x$ | 50 ppm |
| CO | 2.69 ppm |

As per the composition of this gas, a pre-treatment is considered necessary, consisting of substantial elimination of the $SO_x$ content and a reduction in temperature. To do this a counterflow absorption column with NaOH was installed. It is important to stress that, in the procedure of the invention, as well as the reduction in the net balance of $CO_2$, a reduction in the final $NO_x$ concentration (95% NO and the rest $NO_2$) is obtained as a consequence of the dissolution in water of NO and $NO_2$ (especially the latter). As per this treatment, the following gas was added to the photosynthetic reactor:

| | |
|---|---|
| Temperature | 40° C. |
| Pressure | 1.98 bar |
| Density | 2.22 kg/m3 |
| Mass flow | 38,716 kg/h |
| Specific heat | 0.24 kcal/kg |
| Volumetric flow | 17,473 m³/h |
| $CO_2$ | 7.37% V |
| $N_2$ | 85.95% V |
| $O_2$ | 2.95% V |
| $H_2O$ | 3.69% V |
| $CH_4$ | 10,502 ppm |
| $NO_x$ | 58 ppm |
| $SO_2$ | 1 ppm |
| CO | 0 ppm |

The mixture of gases given in the table above, a result of the pre-treatment, was added to the photosynthetic reactors (continually stirred to favour the passage of light and thus made of a transparent material) that contained a monospecific culture of microalgae (specifically a culture of *Dunaliella salina*). as a result, a production of 335 kg/h of biomass was obtained for a plant of 4,100 m³.

To obtain this biomass, firstly 25% of the culture in the reactors was extracted. This culture, having first gone through the centrifuge step (extraction step), passed through an acidification step in a tank with a capacity of 1,500 m³. The basis of this acidification step is the following:

the extracted culture, a result of the continual bubbling of exhaust gases, has a very high $CO_2$, bicarbonate and carbonate content. When the $CO_2$ stops bubbling, the pH of the dissolution tends to rise, displacing the balance towards the formation of carbonates. If a lot of carbonate is formed, it exceeds the solubility point and starts to precipitate. This precipitation could produce problems of fouling, which could in turn lead to contamination and cause complications in the transfer of water. Therefore, given that the mechanical separation (separation step) is not capable of processing all the extracted volume at once, an acid must be added during this storage period. Specifically, a solution of HCl (1M) was added with the aim of maintaining the pH at under 7 at all times.

This extracted culture then passed through the mechanical separation step, which was carried out with a centrifuge, thus obtaining a product with 18% solids.

As well as the concentrated fraction (18% in solids), an aqueous (permeated) fraction was obtained, which represented a total volume of 9,680 m³/day. This water, because it was water from the culture, was loaded with $CO_2$, bicarbonate and carbonate. To release this load from the water, it was alkalised with NaOH to a pH of 9.5 with the aim of displacing the balance towards the formation of carbonate and thus exceed the solubility limit of the carbonate, making it precipitate. Thus, $CO_2$ was chemically taken up, obtaining water with a low $CO_2$, bicarbonate and carbonate content. This water with a low content of these elements was returned to the system (the photobioreactors), with a renewed $CO_2$ uptake capacity. If this water were added without a prior chemical uptake step, the $CO_2$ assimilation capacity of the water would be minimal as it would be close to saturation.

To favour subsequent extraction of the lipid fraction which contains the product of interest (EPA) the solid obtained underwent a disruption step, based on the application of ultrasounds at a frequency of 350 Hz for 8 minutes.

Once disruption had occurred, the lipid fraction was extracted by using a combination of hexane/ethanol (2/1) as the apolar phase (of the lipid fraction) extracting solvent. Once the lipid fraction was extracted, the product of interest (EPA) was purified.

To obtain an EPA of maximum purity (94% richness) a molecular distillation phase was carried out. To do this, firstly, the extracted lipids were saponified and methylated to thus obtain the respective methyl esters (methyl esters are more stable than triglycerides; if triglycerides are added to the molecular distillation phase, degradation occurs). Therefore, thanks to this distillation, the eicosapentaenoic acid ester (eicosapentaenoate) with a purity of 94% was obtained. Thus, after a saponification step, EPA production of 100 kg/day was obtained.

Example Number 2

Obtaining DHA

The starting point is the uptake of greenhouse gases resulting from combustion in a cement factory, these emissions being:

| Temperature | 170° C. |
|---|---|
| Pressure | 1 bar |
| Density | 0.81 kg/m3 |
| Mass flow | 22,000 kg/h |
| Specific heat | 0.25 kcal/kg |
| Volumetric flow | 27,160.49 m³/h |
| $CO_2$ | 7% V |
| $N_2$ | 66.8% V |
| $O_2$ | 1.9% V |
| $H_2O$ | 17.3% V |
| $CH_4$ | 9,000 ppm |
| $NO_x$ | 50 ppm |
| $SO_x$ | 50 ppm |
| CO | 2.69 ppm |

As per the composition of this mixture of gases, the $SO_x$ content was substantially eliminated and the gas temperature reduced. To do this a counterflow absorption column with NaOH was installed.

As per this treatment, a mixture of gases with the following composition was added to the photosynthetic reactor:

| Temperature | 40° C. |
|---|---|
| Pressure | 1.98 bar |
| Density | 2.22 kg/m3 |
| Mass flow | 19,360 kg/h |
| Specific heat | 0.24 kcal/kg |
| Volumetric flow | 8,720.72 m³/h |
| $CO_2$ | 7.37% V |
| $N_2$ | 85.95% V |
| $O_2$ | 2.95% V |
| $H_2O$ | 3.69% V |
| $CH_4$ | 9,600 ppm |
| $NO_x$ | 41 ppm |
| $SO_2$ | 1 ppm |
| CO | 0 ppm |

The mixture of gases given in the table above, a result of the pre-treatment, was added to the photosynthetic reactors (continually stirred to favour the passage of light and thus made of a transparent material) that contained a monospecific culture of microalgae (specifically a culture of *Nannochloropsis Gaditana*). As a result of this procedure, a production of 170 kg/h of biomass was obtained for a plant of 2,040 m³.

To obtain this biomass, firstly 40% of the culture in the reactors was extracted. This culture, having first gone through the mechanical separation step, passed through an acidification step in a tank with a capacity of 1,500 m³. The basis of this acidification step is the following:

the extracted culture, a result of the continual bubbling of exhaust gases, has a very high $CO_2$, bicarbonate and carbonate content. When the $CO_2$ stops bubbling, the pH of the dissolution tends to rise, displacing the balance towards the formation of carbonates. If a lot of carbonate is formed, it exceeds the solubility point and starts to precipitate. This precipitation could produce problems of fouling, which could in turn lead to contamination and cause complications in the transfer of water. Therefore, given that the mechanical separation (separation step) is not capable of processing all the extracted volume at once, an acid must be added during this storage period. Specifically, a solution of HCl (1M) was added with the aim of maintaining the pH at under 7 at all times.

This culture then moved on to the mechanical separation step, which was carried out with a press filter, producing a product with 23% of solids.

Also, an aqueous fraction (supernatant from the decantation tank) was obtained from this product, representing a total volume of 7,026 m³/day. This water, because it was water from the culture, was loaded with $CO_2$, bicarbonate and carbonate. To release this load from the water, it was alkalised with KOH to a pH of 9 with the aim of displacing the balance towards the formation of carbonate and thus exceed the solubility limit of the carbonate, making it precipitate. Thus, $CO_2$ was chemically taken up, obtaining water with a low $CO_2$, bicarbonate and carbonate content. This water with a low content of these elements was returned to the system (the photobioreactors), with a renewed $CO_2$ uptake capacity. If this water were added without a prior chemical uptake step, the $CO_2$ assimilation capacity of the water would be minimal as it would be close to saturation.

The lipid extraction, the fraction in which the product of interest (DHA) is found, was carried out using solvents, specifically a heptane/isopropanol (2/1) mixture. This extraction was performed in a reactor stirred to reflow (the mixture was subjected to 80° C. while stirred; all the solvent that evaporated at this temperature was condensed, dropping back into the reactor).

To obtain DHA with the maximum purity (91% richness) from the lipid extract obtained, an extraction step with $CO_2$ under supercritical conditions was performed: specifically, the conditions were a pressure of 200 bar and a temperature of 35° C. Thus, DHA production was 51 kg/day.

Example Number 3

Obtaining Omega-7 (Palmitoleic Acid)

The starting point is the uptake of greenhouse gases resulting from combustion in a cement factory, these emissions being:

| Temperature | 420° C. |
|---|---|
| Pressure | 1 Bar |
| Density | 0.79 kg/m3 |
| Mass flow | 2,000 kg/h |
| Specific heat | 0.25 kcal/kg |
| Volumetric flow | 2,531.65 m³/h |
| $CO_2$ | 12% V |

-continued

| | |
|---|---|
| N₂ | 61% V |
| O₂ | 1.9% V |
| H₂O | 20.7% V |
| CH₄ | 2,500 ppm |
| NO$_x$ | 90 ppm |
| SO$_x$ | 50 ppm |
| CO | 1.65 ppm |

As per the composition of these emissions, the SO$_x$ content was substantially eliminated and the temperature reduced. To do this a counterflow absorption column with NaOH was installed.

As per this pre-treatment, a mixture of gases with the following composition was added to the photosynthetic reactor.

| | |
|---|---|
| Temperature | 40° C. |
| Pressure | 1.98 Bar |
| Density | 2.22 kg/m3 |
| Mass flow | 1,760 kg/h |
| Specific heat | 0.24 kcal/kg |
| Volumetric flow | 792.79 m³/h |
| CO₂ | 13.5% V |
| N₂ | 63% V |
| O₂ | 2.1% V |
| H₂O | 3.2% V |
| CH₄ | 2,300 ppm |
| NO$_x$ | 92 ppm |
| SO₂ | 2 ppm |
| CO | 0 ppm |

The gases given in the table above, a result of the treatment, were added to the photosynthetic reactors (continually stirred to favour the passage of light and thus made of a transparent material) that contained a plurispecific culture of microalgae (specifically a culture of *Tetraselmis suecica* and *isochrysis galbana*). As a result of this procedure, a production of 27.83 kg/h of biomass was obtained for a plant of 334 m³.

To obtain this biomass, firstly 50% of the culture in the reactors was extracted. This culture, having first gone through the mechanical separation step, passed through an acidification step in a tank with a capacity of 1,500 m³. The basis of this acidification step is the following:

the extracted culture, a result of the continual bubbling of exhaust gases, has a very high CO₂, bicarbonate and carbonate content. When the CO₂ stops bubbling, the pH of the dissolution tends to rise, displacing the balance towards the formation of carbonates. If a lot of carbonate is formed, it exceeds the solubility point and starts to precipitate. This precipitation could produce problems of fouling, which could in turn lead to contamination and cause complications in the transfer of water. Therefore, given that the mechanical separation (separation step) is not capable of processing all the extracted volume at once, an acid must be added during this storage period. Specifically, a solution of HCl (1M) was added with the aim of maintaining the pH at under 7 at all times.

This culture then moved on to the mechanical separation step, which was carried out with a combination of coagulation-flocculation-filtration. It was coagulated with aluminium sulphate, thus neutralising the microalgae load, and was flocculated with a polymer polyelectrolyte (ZETAG). Next, the culture underwent a press filtration process with the aim of increasing the solid content. The cake obtained after this concentration step was a moist biomass with a solid concentration of 31%.

Also, an aqueous fraction (supernatant from the decantation tank) was obtained from this product, representing a total volume of 5,120 m³/day. This water, because it was water from the culture, was loaded with CO₂, bicarbonate and carbonate. To release this load from the water, it was alkalised with KOH to a pH of 9 with the aim of displacing the balance towards the formation of carbonate and thus exceed the solubility limit of the carbonate, making it precipitate. Thus, CO₂ was chemically taken up, obtaining water with a low CO₂, bicarbonate and carbonate content. This water with a low content of these elements was returned to the system (the photobioreactors), with a renewed CO₂ uptake capacity. If this water were added without a prior chemical uptake step, the CO₂ assimilation capacity of the water would be minimal as it would be close to saturation.

The lipid extraction, the fraction in which the product of interest (palmitoleic acid: omega-7) is found, was carried out using isopropanol as the extraction solvent. This extraction was performed in a reactor stirred to reflow (the working temperature was 85° C. while stirred; all the solvent that evaporated at this temperature was condensed, dropping back into the reactor). To obtain omega-7 with the maximum purity (87% richness) an extraction step with CO₂ under supercritical conditions was performed: specifically, the conditions were a pressure of 180 bar and a temperature of 70° C. Thus, omega-7 production was 8.35 kg/day.

In conclusion, by using the procedure of the invention it was possible to not only to produce fatty acids of pharmaceutical and nutritional interest, but also to efficiently take up, convert and revalue CO₂ from among other greenhouse gases (NO$_x$, CH₄, etc.), thus producing an overall reduction in CO₂ emitted into the atmosphere, making it a beneficial and sustainable process for the environment.

The invention claimed is:
1. Procedure for obtaining fatty acids of pharmacological and nutritional interest comprising the steps of:
   a) feeding a gas or mixture of gases comprising CO₂ into a reactor containing a culture that comprises at least one species of microalgae capable of photosynthesis;
   b) photosynthesis by the species of microalgae using the CO₂ supplied, producing a biomass containing the general formula (I) compound:

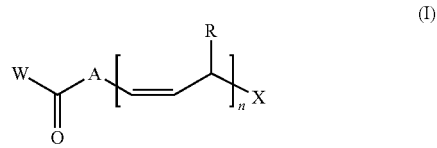

wherein:
   A and X are equal or different independently and are selected from alkyl C$_3$-C$_{10}$, alkenyl C$_1$-C$_{10}$, cycloalkyl C$_1$-C$_7$ or any substituted or unsubstituted aryl group;
   n is an integer from 1 to 10;
   R is selected from H, a hydroxyl group, alkyl C$_1$-C$_4$, alkenyl C$_1$-C$_3$, cycloalkyl C$_3$-C$_7$ or any substituted or unsubstituted aryl group;
   W is selected from the group consisting of a hydroxyl group, a glycerol molecule bound to an additional general formula (I) compound forming a diglyceride, or a glycerol molecule bound to two additional general formula (I) compounds forming a triglyceride;
   and their salts, preferably any pharmaceutically acceptable salt, solvates and their prodrugs;

c) extraction of the general formula (I) compound from the biomass obtained in step b); and
d) concentration and/or purification of the general formula (I) compound from the extract obtained in step c); characterised in that, after the photosynthesis step, between 5 and 100% of the culture is removed from the reactor, which is then separated in a solid fraction that contains biomass, which biomass subsequently undergoes the step of extracting the general formula (I) compound and a liquid phase fraction that contains carbonates and/or bicarbonates, which are separated from the liquid fraction, after which the liquid fraction substantially free of carbonates and/or bicarbonates is then returned at least partially to the reactor.

2. Procedure according to claim 1, in which in the step in which the culture is at least partially removed from the reactor, between 5 and 50% of the culture is removed.

3. Procedure according to claim 2, in which in the step in which the culture is at least partially removed from the reactor, approximately 10% of the culture is removed.

4. Procedure according to claim 1, in which before step a) a pre-treatment is carried out with the gas or a mixture of gases comprising $CO_2$ which consists of at least one of substantial elimination of $SO_x$, $NO_x$ and moisture and changing the gas temperature to a range of 30 to 40° C.

5. Procedure according to claim 1, in which the microalgae is selected from the group consisting of: *Clorophyceae, Bacilliarioficeas, Dinophyceae, Cryptophyceae, Chrysophyceae, Haptophyceae, Prasinophyceae, Raphidophyceae, Eustigmatophyceae* or any combination thereof.

6. Procedure according to claim 5, in which the species of microalgae is selected from the group consisting of *Dunaliella salina, Tetraselmis Galvana, Tetraselmis suecica, Iisochrysis galbana, Nannochloropsis Gaditana* o *Nannochloris*, in any combination thereof.

7. Procedure according to claim 1, in which the gas or mixture of gases that is fed into the reactor in step a) comes exogenously, from the atmosphere or any industry and, endogenously, from the gases generated during the procedure itself, in any combination thereof.

8. Procedure according to claim 7, in which the exogenous fraction of the gas or mixture of gases that is fed into the reactor in step a) comes from a cement factory.

9. Procedure for obtaining fatty acids according to claim 1, in which in step b) the culture undergoes turbulence and is exposed to natural and/or artificial light in any combination.

10. Procedure according to claim 1, in which after the step in which the culture is at least partially removed from the reactor, the removed culture is acidified to a pH between 3.5 and 8.

11. Procedure according to claim 10, in which the removed culture is acidified to a pH between 6 and 8.

12. Procedure according to claim 10, in which the acidification is performed by adding to the culture at least one acidifying agent selected from the group consisting of $CO_2$, a mixture of $CO_2$ and air, strong or weak acids or any combination of these.

13. Procedure according to claim 12, in which the acidification is carried out by adding a mixture of $CO_2$ and air to the culture.

14. Procedure according to claim 1, in which after the step of at least partially removing the culture from the reactor, the separation of the solid fraction that contains biomass and the liquid fraction that contains carbonates and/or bicarbonates is carried out by at least one technique selected from the group consisting of filtration, centrifugation, flocculation, electrocoagulation, ultrasounds, evaporation, decantation or any combination of these.

15. Procedure according to claim 1, in which the separation of carbonates and/or bicarbonates of the liquid fraction resulting from at least partial removal of the culture from the reactor is carried out by precipitation of the corresponding carbonated salts caused by the addition of at least one alkali.

16. Procedure according to claim 1, in which before step c) a sub-step of lysis of the algae cells is applied to the culture.

17. Procedure according to claim 16, in which lysis is performed by means of ultrasounds at frequencies between 100 and 1,000 Hz.

18. Procedure according to claim 16, in which lysis is performed by means of cavitation at pressures of between 250 and 1,200 bar.

19. Procedure according to claim 16, in which the lysis is carried out by means of altering the culture pH to values under 6 or over 9 with acids or bases.

20. Procedure according to claim 16, which is repeated 1 to 5 times before step c).

21. Procedure according to claim 1, in which in step c) the extraction is carried out by means of a technique selected from the group consisting of extraction with organic solvents, extraction under supercritical conditions or a combination of these.

22. Procedure according to claim 21, in which the extraction is carried out using organic solvents.

23. Procedure according to claim 21, in which the organic solvents are a 2:1 mixture of hexane:ethanol.

24. Procedure according to claim 1, in which step d) is carried out by means of a technique selected from the group consisting of molecular or fractioned distillation, enzyme division, supercritical extraction with $CO_2$, crystallisation at low temperatures, adsorption chromatography, precipitation with urea or any combination of these.

25. Procedure according to claim 1, wherein the $CO_2$ containing gas is a gas from a cement factory.

26. Procedure according to claim 1, in which before adding to the reactor the gas undergoes at least one of the following treatments: substantial elimination of $SO_x$, $NO_x$ and moisture and adjusting its temperature to a range of 30 to 40° C.

* * * * *